(12) United States Patent
Berger et al.

(10) Patent No.: US 11,291,487 B2
(45) Date of Patent: Apr. 5, 2022

(54) SCREW FIXATION DEVICE, FIXATION KIT AND FIXATION METHOD

(71) Applicant: AZURMEDS INC., Chicago (IL)

(72) Inventors: Jean-Marie Berger, Eden Prairie, MN (US); Pierric Deransart, Saint martin d'Uriage (FR); Christopher R. Chuinard, Traverse City, MI (US); Thomas Bradley Edwards, Houston, TX (US); Grant E. Garrigues, Hinsdale, IL (US); Armodios M. Hatzidakis, Denver, CO (US); Gregory P. Nicholson, Western Spring, IL (US); Felix Buddy Savoie, New Orleans, LA (US)

(73) Assignee: AZURMEDS INC., Dallas, TX (US)

( * ) Notice: Subject to any disclaimer, the term of this patent is extended or adjusted under 35 U.S.C. 154(b) by 153 days.

(21) Appl. No.: 16/724,886

(22) Filed: Dec. 23, 2019

(65) Prior Publication Data

US 2020/0205869 A1 Jul. 2, 2020

Related U.S. Application Data

(60) Provisional application No. 62/783,780, filed on Dec. 21, 2018.

(51) Int. Cl.
| | | |
|---|---|---|
| *A61B 17/86* | (2006.01) | |
| *A61B 17/17* | (2006.01) | |
| *A61B 17/16* | (2006.01) | |
| *A61B 17/68* | (2006.01) | |
| *A61B 17/88* | (2006.01) | |
| *A61B 34/10* | (2016.01) | |
| *A61F 2/30* | (2006.01) | |

(Continued)

(52) U.S. Cl.
CPC ........ *A61B 17/863* (2013.01); *A61B 17/1635* (2013.01); *A61B 17/1684* (2013.01); *A61B 17/1778* (2016.11); *A61B 17/68* (2013.01); *A61B 17/864* (2013.01); *A61B 17/8605* (2013.01); *A61B 17/8635* (2013.01); *A61B 17/8866* (2013.01); *A61B 34/10* (2016.02); *A61F 2/30749* (2013.01); *A61F 2/40* (2013.01); *A61B 2017/681* (2013.01); *A61B 2034/105* (2016.02); *A61F 2002/2835* (2013.01)

(58) Field of Classification Search
CPC ... A61B 17/86; A61B 17/8605; A61B 17/861; A61B 17/8615; A61B 17/8625; A61B 17/863; A61B 17/8635; A61B 17/864; A61B 17/8645; A61B 17/866
See application file for complete search history.

(56) References Cited

U.S. PATENT DOCUMENTS

| | | |
|---|---|---|
| 4,175,555 A | 11/1979 | Herbert |
| 4,463,753 A | 8/1984 | Gustilo |
| 4,537,185 A | 8/1985 | Stednitz |

(Continued)

*Primary Examiner* — Eric S Gibson
(74) *Attorney, Agent, or Firm* — Nixon & Vanderhye

(57) ABSTRACT

Disclosed is a bone screw fixation device including two screws and only two. The bone screw includes: a first screw provided at its proximal end with a head for compressing the bone by an end-abutment; and a second screw provided at its distal end with a bone threading having a first helix pitch and at its proximal end with a bone threading having a helix with a pitch smaller than the first helix pitch.

20 Claims, 6 Drawing Sheets

(51) Int. Cl.
*A61F 2/40* (2006.01)
*A61F 2/28* (2006.01)

(56) References Cited

U.S. PATENT DOCUMENTS

| | | | |
|---|---|---|---|
| 4,858,601 A * | 8/1989 | Glisson | A61B 17/8685 |
| | | | 606/916 |
| 5,019,079 A * | 5/1991 | Ross | A61B 17/863 |
| | | | 411/389 |
| 5,259,398 A * | 11/1993 | Vrespa | A61B 17/863 |
| | | | 128/898 |
| 5,334,204 A | 8/1994 | Clewett et al. | |
| 5,403,136 A | 4/1995 | Mathys | |
| 5,536,127 A * | 7/1996 | Pennig | A61B 17/863 |
| | | | 411/397 |
| 5,925,048 A | 7/1999 | Ahmad et al. | |
| 6,030,162 A * | 2/2000 | Huebner | A61B 17/1682 |
| | | | 411/263 |
| 6,306,140 B1 * | 10/2001 | Siddiqui | A61B 17/863 |
| | | | 606/315 |
| 6,565,573 B1 | 5/2003 | Ferrante et al. | |
| 7,037,309 B2 * | 5/2006 | Weil | A61B 17/863 |
| | | | 606/304 |
| 7,517,350 B2 * | 4/2009 | Weiner | A61B 17/8605 |
| | | | 606/105 |
| 7,637,929 B2 | 12/2009 | Auth | |
| 7,708,738 B2 * | 5/2010 | Fourcault | A61B 17/8635 |
| | | | 606/67 |
| 8,900,279 B2 | 12/2014 | Assell et al. | |
| 8,945,193 B2 * | 2/2015 | Kirschman | A61B 17/8841 |
| | | | 606/304 |
| 8,992,587 B2 * | 3/2015 | Kirschman | A61B 17/863 |
| | | | 606/305 |
| 9,011,505 B2 * | 4/2015 | Prandi | A61B 17/8635 |
| | | | 606/315 |
| 9,265,540 B2 * | 2/2016 | Kirschman | A61B 17/7098 |
| 9,504,504 B2 * | 11/2016 | Prandi | A61B 17/8635 |
| 9,636,230 B2 * | 5/2017 | Talwar | A61F 2/30771 |
| 9,968,391 B2 * | 5/2018 | Cook | A61B 17/863 |
| 10,130,407 B2 * | 11/2018 | Castaneda | A61B 17/8888 |
| 10,349,992 B2 * | 7/2019 | Varner | A61B 17/863 |
| 11,020,159 B2 * | 6/2021 | Varner | A61B 17/809 |
| 2003/0045881 A1 * | 3/2003 | Barouk | A61B 17/863 |
| | | | 606/304 |
| 2004/0068261 A1 * | 4/2004 | Fourcault | A61B 17/863 |
| | | | 606/67 |
| 2007/0233123 A1 * | 10/2007 | Ahmad | A61B 17/863 |
| | | | 606/307 |
| 2007/0233125 A1 * | 10/2007 | Wahl | A61B 17/8605 |
| | | | 606/250 |
| 2008/0234763 A1 * | 9/2008 | Patterson | A61B 17/863 |
| | | | 606/315 |
| 2010/0174323 A1 * | 7/2010 | Fourcault | A61B 17/863 |
| | | | 606/304 |
| 2011/0276095 A1 * | 11/2011 | Bar | A61B 17/863 |
| | | | 606/279 |
| 2011/0313473 A1 * | 12/2011 | Prandi | A61B 17/863 |
| | | | 606/315 |
| 2012/0022603 A1 * | 1/2012 | Kirschman | A61B 17/863 |
| | | | 606/305 |
| 2012/0197311 A1 * | 8/2012 | Kirschman | A61B 17/7098 |
| | | | 606/304 |
| 2013/0053964 A1 * | 2/2013 | Talwar | A61F 2/442 |
| | | | 623/17.16 |
| 2013/0211468 A1 * | 8/2013 | Huebner | A61B 17/863 |
| | | | 606/328 |
| 2014/0135851 A1 * | 5/2014 | Cook | A61B 17/863 |
| | | | 606/309 |
| 2016/0354074 A1 * | 12/2016 | Miller | A61B 17/863 |
| 2017/0196608 A1 * | 7/2017 | Castaneda | A61B 17/863 |
| 2018/0263669 A1 * | 9/2018 | Peterson | A61B 17/7225 |
| 2020/0205869 A1 * | 7/2020 | Berger | A61B 17/8866 |

* cited by examiner

[Fig. 1]
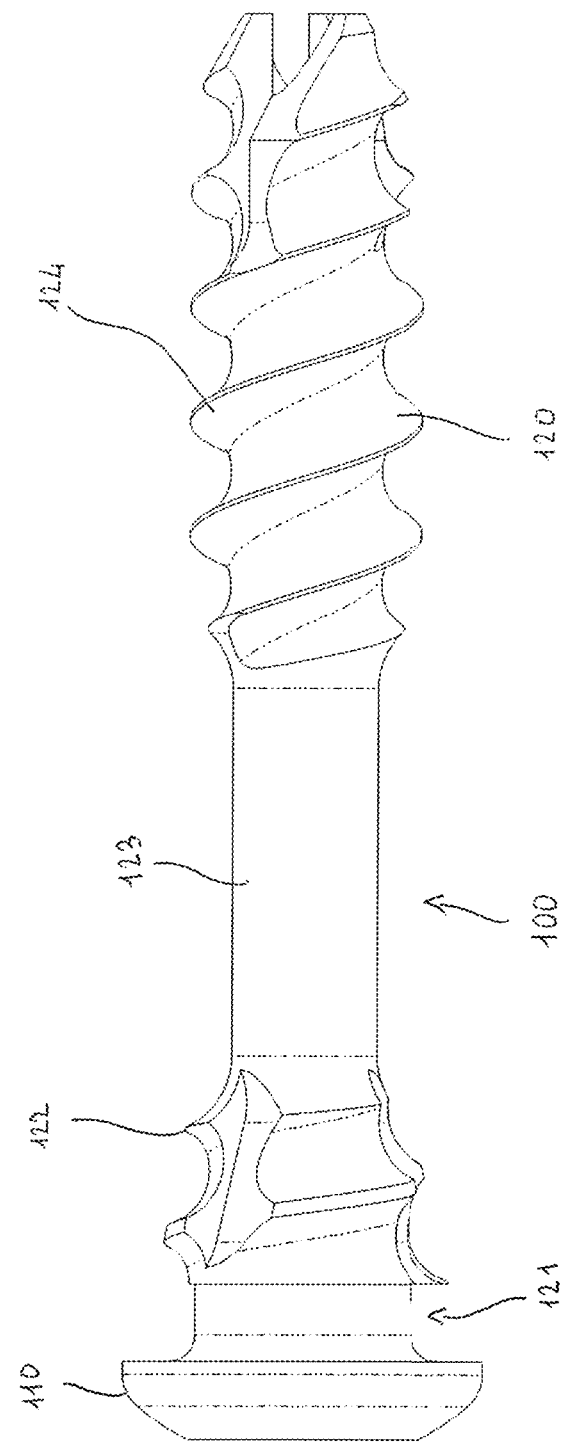

[Fig. 2]
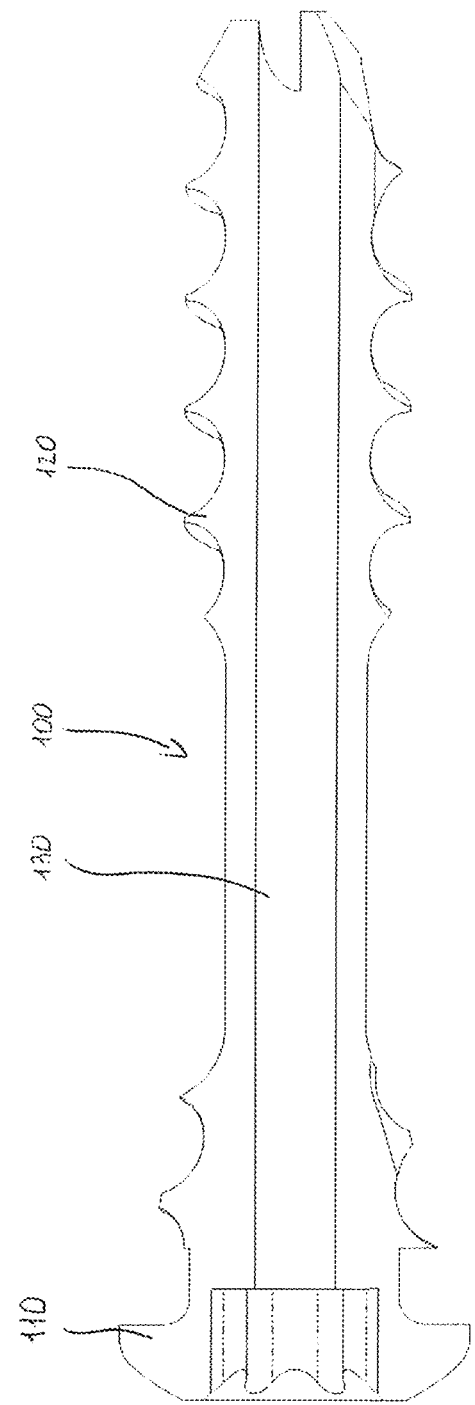

[Fig. 3]
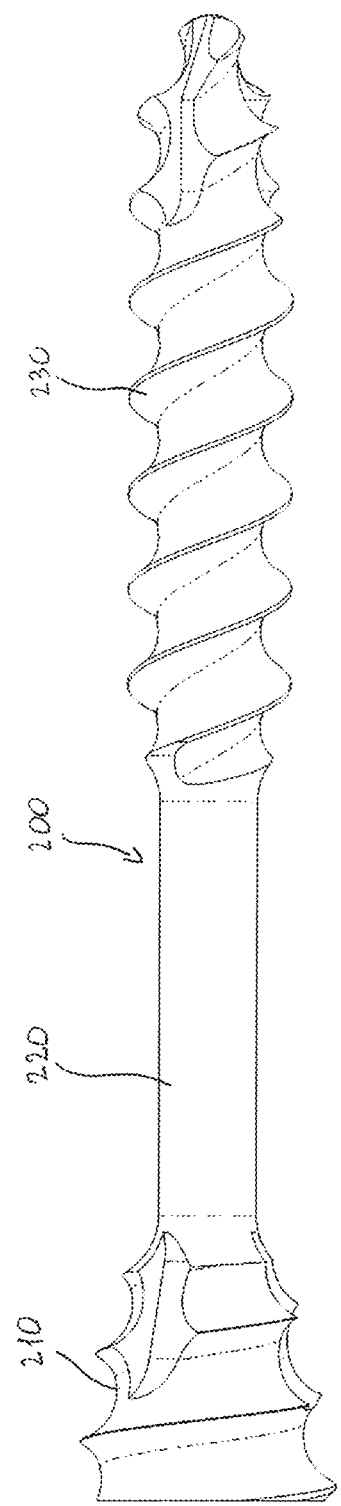

[Fig. 4]
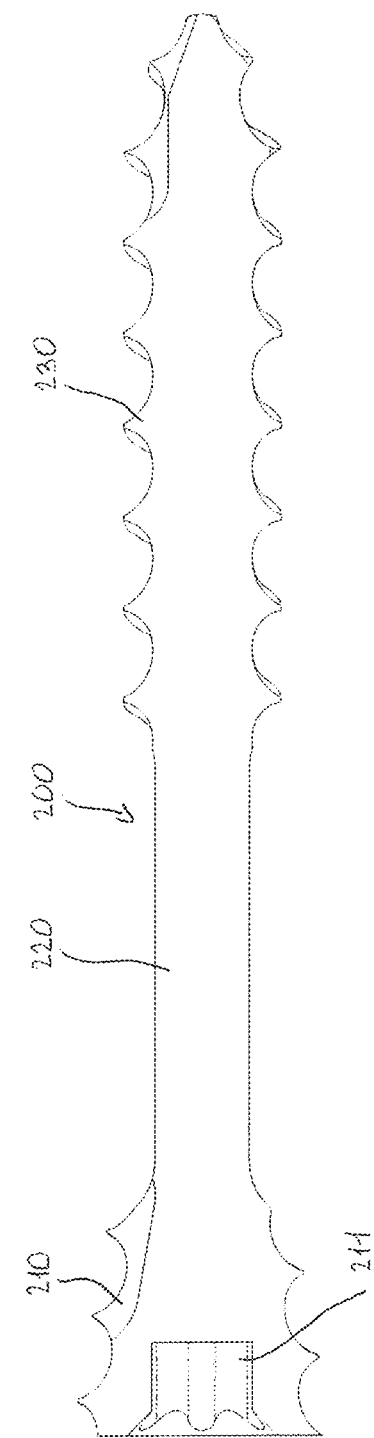

[Fig. 5]
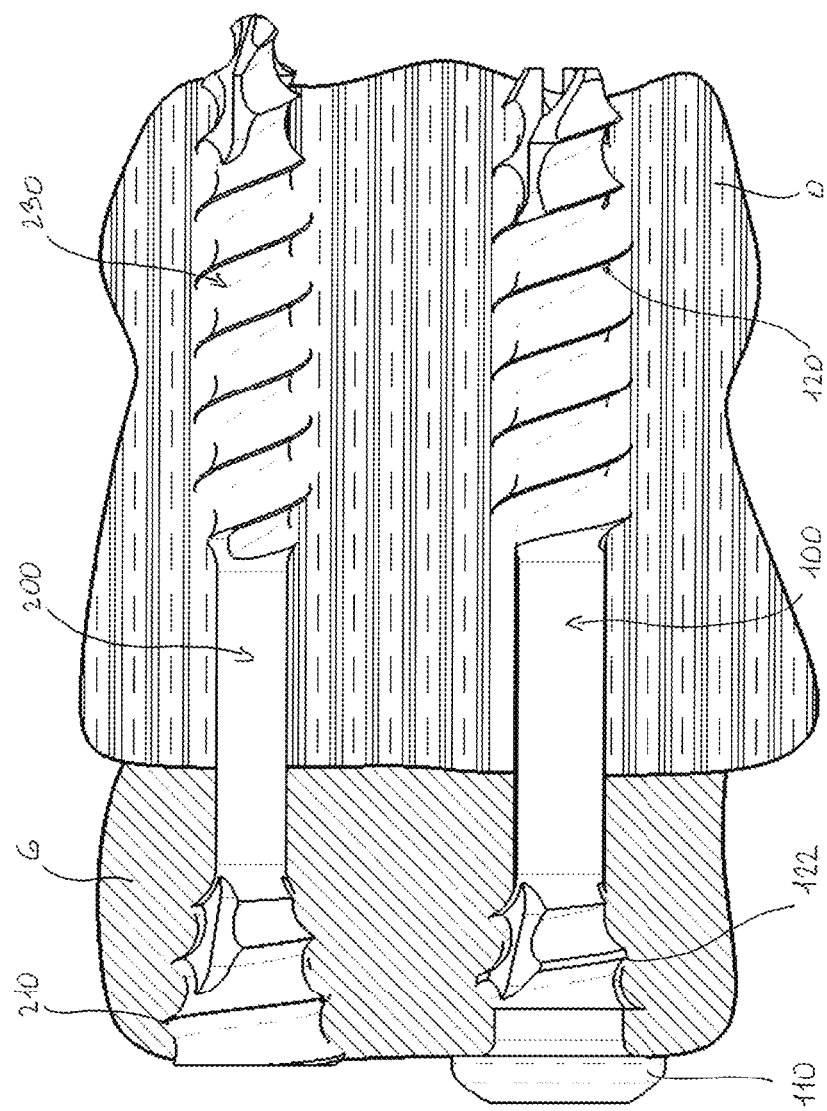

[Fig. 6]
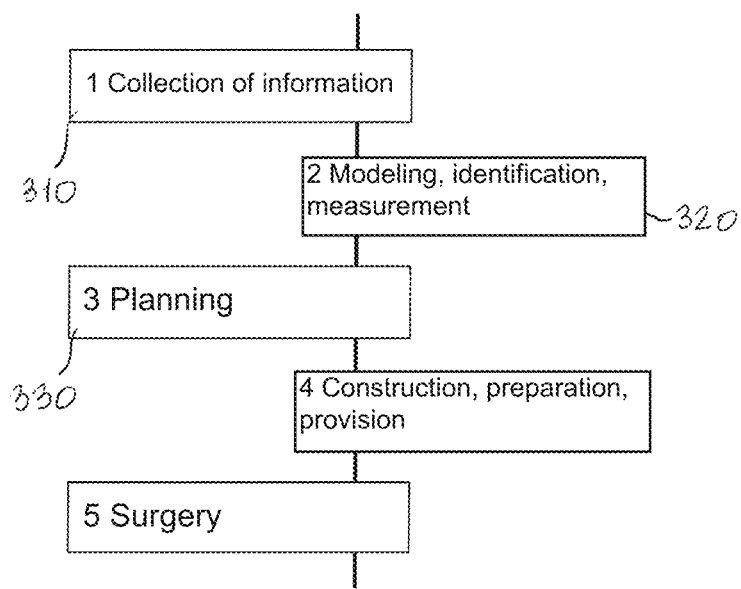

SCREW FIXATION DEVICE, FIXATION KIT AND FIXATION METHOD

FIELD OF APPLICATION OF THE INVENTION

The invention relates to the fixation by screws in bones and in particular to the adaptations allowing to optimize this fixation.

DESCRIPTION OF THE PRIOR ART

There is a plurality of situations where screws are introduced for purposes of fixation of one portion of bone to another portion of bone. For example, as part of an abutment procedure for the treatment of shoulder instabilities, there is a fixation device composed of two screws ensuring the fixation of a bone graft (from the cutting of the coracoid, operation called Latarjet operation, or other sample—outer quarter of the clavicle, iliac crest- or -distal tibia-allograft or formed by a block of bone substitute) forming an abutment on the injured edge of the glenoid surface of the scapula.

Among the screws proposed for this type of fixation, there are headless screws and head screws. To differentiate them, a head screw is considered to be pre-formed with a protruding proximal portion, relative to the shaft, which is smooth blocking the advancement of the screw in the bone whereas a headless screw does not have this smooth blocking protruding portion. The rear portion of the screw located at one end of the screw and pre-formed with a means for cooperation with the setting tool is called proximal portion. The distal portion is the front portion of the screw located at the other end and coming into contact first with the part to be fixed.

These screws are conventionally used for this type of application by pair of screws with the same features.

Among the headless screws, there are those described in documents U.S. Pat. Nos. 4,175,555, 4,463,753, 5,403,136, 6,306,140 and U.S. Ser. No. 10/130,407.

The fixation device comprising such screws has several disadvantages, among these disadvantages:
  The complexity of the revision (that is to say of removing the fixation) due to the difficulty of identifying the proximal portion of the screw and the difficulty of inserting the setting tool in the cooperation means (burial of the cooperation means in the bone);
  To obtain adequate compression, there is a risk of incorrect positioning of the screw (protrusion of the screw forward of the graft or rearward of the scapula), with consequently:
  Risk of injuring anatomical structures (muscle, nerve);
  Risk of loss of the graft fixation if one of the screws passes through the graft;
  To obtain an adequate positioning of the screw, a risk of insufficient or excessive compression (because it depends on the bone quality and the driving of the screw) with consequently:
  Risk of loss of the graft fixation and mobilization of the graft in case of insufficient compression;
  Risk of graft fracture in the event of over-compression.

Among the head screws, there are those described in the following documents: U.S. Pat. Nos. 4,537,185, 5,334,204, 5,925,048, 6,565,573, 7,637,929 and 8,900,279.

The device comprising such screws has disadvantages, among these disadvantages:
  With heads that are partially or totally buried in the graft (hemispherical head):
  A risk of graft fracture (too small bone section between the two screw heads or too small bone section between the screw head and the end of the graft);
  The complexity of the revision due to the difficulty of identifying the screw head and the difficulty of inserting the setting tool in the cooperation means (burial of the cooperation means in the bone).
  With heads that are partially or totally protruding from the graft (flat or domed head):
  A risk of irritation of the soft tissues (muscles, ligaments, nerves, etc.) by friction on the screw head.
  A risk of conflict between the two screw heads (indeed the diameter of the screw heads dictates the center distance which can prove to be too large relative to the size of the bone graft, especially in the case of a small graft) with consequently:
  Risk of graft fracture (too small bone section between the head of the second screw and the end of the graft);
  Risk of insufficient compression at the second screw (overlapping of the screw heads);
  Risk of malpositioning the first screw (during compression of the second screw, displacement of the first screw which can generate a loss of the screw fixation and/or a damage to the graft);

BRIEF DESCRIPTION OF THE INVENTION

Noticing this, the applicant has conducted research aiming at proposing an alternative fixation device solving the disadvantages of the prior art.

These research resulted in the design of a bone screw fixation device comprising two screws and only two, remarkable in that it comprises:
  A first screw provided at its proximal end with a head for compressing the bone by an end-abutment;
  A second screw provided at its distal end with a bone threading having a first helix pitch and at its proximal end with a bone threading having a helix with a pitch smaller than the first helix pitch.

The difference in pitch between the distal and proximal threadings of the second screw allows having the desired compression.

This device is intended for fixing without a plate a bone graft in the shoulder for the purposes of treating pathologies related to the shoulder instability.

This device is more particularly intended for fixing the bone graft in the context of a Lartajet procedure.

This feature is particularly advantageous in that the combined use of a head screw and a headless screw guarantees:
  The optimal position of the two screws independent of the size and the shape of the graft;
  An optimal compression of the graft obtained by the bearing of the head screw on the graft and by the difference in pitch between the distal thread and the proximal thread of the headless screw;
  The absence of risk of conflict between the two proximal portions of the screws, one being buried in the graft and the other being protruding from the graft;
  A control of the risk of graft fracture since the first compression is given by the head screw. The risk of exerting an excessive compression with the headless screw is therefore reduced.

The head screw is generally placed first, in particular for the reasons mentioned above. In addition, it is generally the screw located in the lowest position that is installed first.

According to another particularly advantageous feature of the invention, at least one of the screws comprises a cannula, that is to say that the screw is provided with a longitudinal through hole, According to another particularly advantageous feature of the invention, the head screw comprises:
- a distal threaded portion (at a distance from the head) threaded according to a first pitch,
- a proximal threaded portion (close to the head) threaded according to a second pitch smaller than the first pitch.

According to another particularly advantageous feature, at least one of the screws comprises a conical proximal threaded portion.

According to another particularly advantageous feature, the two screws comprise a conical proximal threaded portion.

According to another particularly advantageous feature of the invention, the conicity of the proximal portion of the two screws has a half angle of about 10 degrees.

According to another particularly advantageous feature of the invention, the proximal portion of at least one screw includes a smooth portion.

According to another particularly advantageous feature of the invention, the smooth portion is pre-formed on the head screw between the head and the threaded proximal portion and has a diameter less than the largest diameter of the threaded proximal portion.

According to another particularly advantageous feature of the invention, the device comprises the two following screws:

A first head screw
including
a cannula, that is to say that the screw is provided with a longitudinal through hole of a diameter comprised between 1 and 2 millimeters,
a head of a diameter comprised between 6 and 9 millimeters and a thickness at the center comprised between 1 and 3 millimeters,
a distal threaded portion (at a distance from the head) threaded according to a first pitch and of an outer diameter comprised between 3 and 5 millimeters;
a conical proximal threaded portion (close to the head) threaded according to a second pitch smaller than the first pitch;
a second headless screw
including
a distal threaded portion threaded according to a first pitch and of an outer diameter comprised between 3 and 5 millimeters,
a conical proximal threaded portion threaded according to a second pitch smaller than the first pitch.

According to a preferred but non-limiting embodiment, the threadings of the distal portions of the screws are multiple threadings and the threadings of the proximal portions are single threadings.

According to another particularly advantageous feature of the invention, the two screws have a smooth middle portion separating the proximal portion from the distal portion.

According to another particularly advantageous feature of the invention, the length of the distal threaded portion forms between 46 and 56 percent of the total length of the head screw and forms between 48 and 58 percent of the total length of the headless screw.

This proportion is defined so that the distal threaded portion is engaged only and solely in the host bone and in no case in the graft, this to allow the compression.

According to another particularly advantageous feature of the invention, the length of the proximal threaded portion of the two screws has a length of 5 to 10 millimeters.

This length is defined so that the proximal threaded portion is engaged only and solely in the graft and in no case in the host bone, this to allow the compression.

The invention also relates to a fixation kit formed of the device described above, namely that the two screws of different designs are packaged in a same package. Thus, according to another particularly advantageous feature, the device is remarkable in that it comprises two screws of different designs which are packaged in a same package for purposes of creating a ready-to-use fixation kit.

According to a particularly advantageous embodiment of the invention, the kit consists of two screws with a length difference comprised between 0.5 and 5.5 millimeters.

According to one embodiment, the kits are delivered non-sterile in a packaging adapted to the sterilization by the care facility.

According to another embodiment, the kits are delivered sterile in a packaging adapted to the sterilization by gamma ray or x-ray and adapted to an aseptic transfer of the device.

According to another particularly advantageous feature, the fixation kit contains screws which have been selected and/or sized specifically for one patient according to a preoperative planning established based on the preoperative imaging of the patient.

The invention also relates to a bone screw provided at its proximal end with a head for compressing the bone by an end-abutment, at its distal end with a bone threading according to a first pitch, remarkable in that it comprises under the head a proximal smooth portion and that it comprises under the proximal smooth portion a proximal threaded portion threaded according to a second pitch smaller than the first pitch.

According to another feature, the proximal threaded portion of said screw is conical.

According to another feature, the distal threaded portion of said screw includes a multiple thread.

According to another feature the proximal smooth portion of said screw has a diameter less than the largest diameter of the proximal threaded portion.

The invention also relates to a method for fixing a bone graft on a shoulder bone remarkable in that it uses two screws and only two adopting the features described above taken together or separately.

Thus, this method applies to a fixation procedure called "Latarjet" procedure.

According to another particularly advantageous feature, the method comprises before the selection and the use of the screws, a preoperative planning including the following operations:
   Collection of a preoperative imaging of the shoulder of the patient by radiography and/or ultrasound and/or CT image and/or MRI of the shoulder,
   Modeling of the joint,
   Identification of at least one anatomical structure,
   Preoperative planning of at least one of the following elements: sizing the graft, positioning the graft, positioning the screws, According to another particularly advantageous feature, the preoperative planning method includes, between the identification and planning operation, an operation of measuring at least one specific feature of the joint of the patient.

The fundamental concepts of the invention having just been exposed above in their most elementary form, other details and features will emerge more clearly upon reading the description that follows and with reference to the appended drawings, giving by way of a non-limiting example, an embodiment of the invention.

BRIEF DESCRIPTION OF THE DRAWINGS

FIG. 1 is an external side view of an embodiment of a first one of the two screws of the device of the invention;

FIG. 2 is a sectional side view of the screw of FIG. 1;

FIG. 3 is an external side view of an embodiment of the second one of the two screws of the device of the invention;

FIG. 4 is a sectional side view of the screw of FIG. 3;

FIG. 5 is a sectional view of an assembly of a bone graft to another bone.

FIG. 6 is a diagram of the main phases of the process leading to the selection and/or the creation of a kit and/or screws according to the invention specific to a patient.

DESCRIPTION OF A PREFERRED EMBODIMENT

An embodiment of the device of the invention consists of the two illustrated screws.

The first screw 100 of FIGS. 1 and 2 comprises a head 110 and a rod 120. The head 110 comprises a recess 111 to cooperate with a setting tool (not illustrated) allowing the insertion of the screw into the bone. This first screw is pre-formed by a cannula 130.

The rod 120 is divided into several portions:

A smooth proximal portion 121 disposed under the head 110,

A conical proximal threaded portion 122 having a given pitch (single thread and disposed under the smooth proximal portion 121), A smooth middle portion 123, A distal threaded portion 124 having a pitch larger (double thread) than the pitch of the proximal portion 122.

The second screw 200 of FIGS. 3 and 4 is formed of a solid headless body which comprises A conical proximal threaded portion 210 having a given pitch (single thread) and a recess 211 to cooperate with a setting tool, A smooth middle portion 220, A distal threaded portion 230 having a pitch larger (double thread) than the pitch of the proximal portion 210.

As illustrated in the drawing of FIG. 5, the device is used for fixing the bone graft G to a host bone O. As illustrated, the screws are sized so that:

the proximal threaded portions 122 and 210 cooperate only with the graft G;

the distal threaded portions 124 and 230 cooperate only with the host bone O.

In addition, the length of the screws 100 and 200 is defined so that the distal threaded portions 124 and 230 of the screws pass through the cortical wall, of the host bone O, opposite the bone graft G.

Prior to the surgical intervention, during the phase of collecting data 310, the preoperative imaging of the patient to be operated is acquired in various ways. For example, radiographies and/or ultrasounds and/or CT images and/or MRI of the shoulder are used.

Based on the preoperative imaging of the patient to be operated, during a modeling and identification phase 320, at least one segmentation and treatment algorithm allows modeling the joint of the patient, identifying at least one anatomical structure. This phase may include the measurement of at least one specific feature of the joint of the patient.

During the planning phase 330, the surgeon performs a preoperative planning by means of a computer interface allowing to view the modeling of the joint and to perform at least one of the following operations: sizing the graft, positioning the graft on the host bone and positioning and selecting the screws constituting the fixation device according to the invention.

This method may further include the constitution, manufacture and provision for the surgical intervention of a patient-specific fixation kit produced based on the previously collected data and, particularly, on the planning output data.

It is understood that the device which has just been described and represented above, has been for the purpose of disclosure rather than limitation. Of course, various arrangements, modifications and improvements can be made to the example above, without departing from the scope of the invention.

The invention claimed is:

1. A bone screw fixation device comprising two screws and only two screws, comprising:
a first screw provided at a proximal end with a head for compressing a bone by an end-abutment,
the head comprising an upper side, a lower side having a bone abutment surface, and a lowermost region with an exteriorly arcuate shape extending from the bone abutment surface,
a proximal smooth portion located under the head and extending from the lowermost region of the head, the proximal smooth portion having a flat exterior surface free of any curved region,
a conical proximal threaded portion located under the proximal smooth portion, wherein
a diameter of the proximal smooth portion is less than a maximum diameter of an exterior diameter of the conical proximal threaded portion, and
the first screw is a single monobloc piece; and
a second screw provided at a distal end with a bone threading having a first helix pitch and at a proximal end with a bone threading having a helix with a pitch smaller than the first helix pitch, the second screw being headless.

2. The fixation device according to claim 1, wherein
the first screw further comprises a distal threaded portion threaded according to a first pitch, and
the conical proximal threaded portion of the first screw is threaded according to a second pitch smaller than the first pitch.

3. The fixation device according to claim 2, wherein a conicity of the proximal portion of the two screws has a half angle of 10 degrees.

4. The fixation device according to claim 1, wherein the second screw comprises a conical proximal threaded portion.

5. The fixation device according to claim 1, wherein the two screws comprise a conical proximal threaded portion.

6. The fixation device according to claim 5, wherein
the conical proximal threaded portion of each of the two screws has a length of 5 to 10 mm.

7. The fixation device according to claim 1, wherein the two screws have a smooth middle portion.

8. The fixation device according to claim 1, wherein,
the two screws each have a distal threaded portion, and
the distal threaded portion of the two screws forms between 46 and 58 percent of a total length of each of the two screws.

9. The fixation device according to claim 1, wherein at least one of the first and second screws comprises a cannula defining a longitudinal through hole.

10. The fixation device according to claim 1, wherein the first screw further comprises:
a recess operative to cooperate with a setting tool allowing insertion of the screw into the bone, the recess extending from the upper side of the head into an interior of the lowermost region of the head and into an interior of the proximal smooth portion,
the conical proximal threaded portion being threaded according to a first pitch,
a smooth middle portion located under the proximal threaded portion, the smooth middle portion free of any threading, and
a distal end located under the smooth middle portion, the distal end being provided with a bone threading according to a second pitch, wherein
the second pitch is larger than the first pitch.

11. The fixation device according to claim 1, wherein the first screw has a distal threaded portion that includes a multiple threading.

12. The fixation device according to claim 1, wherein the total length difference between the two screws is comprised between 0.5 and 5.5 millimeters.

13. A fixation kit formed of the device according to claim 1, wherein said screws have been previously sterilized.

14. A fixation kit formed of the device according to claim 1, wherein the screws are previously selected and/or manufactured based on a preoperative planning.

15. A method for fixing a bone graft on a shoulder bone, the method using two screws and only two where each screw has a different design according to claim 1.

16. A bone screw comprising:
a proximal end provided with a head, the head for compressing a bone by an end-abutment,
the head comprising an upper side, a lower side having a bone abutment surface, and a lowermost region with an exteriorly arcuate shape extending from the bone abutment surface,
a proximal smooth portion located under the head and extending from the lowermost region of the head, the proximal smooth portion having a flat exterior surface free of any curved region,
a conical proximal threaded portion located under the proximal smooth portion, the conical proximal threaded portion being threaded according to a first pitch,
a smooth middle portion located under the proximal threaded portion, the smooth middle portion free of any threading, and
a distal end located under the smooth middle portion, the distal end being provided with a bone threading according to second pitch, wherein,
the second pitch is larger than the first pitch,
a diameter of the proximal smooth portion is less than a maximum diameter of an exterior diameter of the conical proximal threaded portion, and
the head, the proximal smooth portion, conical proximal threaded portion, the smooth middle portion, and the distal end are a single monobloc piece.

17. The screw according to claim 16, further comprising a cannula extending through the smooth proximal portion, the conical proximal threaded portion, the smooth middle portion, and the distal end.

18. The screw according to claim 16, wherein,
the conical proximal threaded portion is a single threading, and
the bone threading of the distal end includes a multiple thread.

19. The screw according to claim 16, further comprising a recess operative to cooperate with a setting tool allowing insertion of the screw into the bone, the recess extending from the upper side of the head into an interior of the lowermost region of the head and into an interior of the proximal smooth portion.

20. A method for fixing a bone graft on a shoulder bone, the method using two screws, the method comprising:
using a first screw provided at a proximal end with a head for compressing a bone by an end-abutment;
using a second screw provided at a distal end with a bone threading having a first helix pitch and at a proximal end with a bone threading having a helix with a pitch smaller than the first helix pitch; and
before selection and the use of the first and second screws, a preoperative planning including the following operations:
collecting a preoperative imaging of a shoulder of the patient by radiography and/or ultrasound and/or CT image and/or MRI of the shoulder,
modelling a joint,
identifying at least one anatomical structure, and
preoperative planning of at least one of the following operations: sizing the graft, positioning the graft on the host bone and positioning the screws.

* * * * *